United States Patent
Porat

[11] Patent Number: 5,873,890
[45] Date of Patent: Feb. 23, 1999

[54] SYSTEM FOR PREVENTION OF BLOOD SPURTS FROM BLOOD VESSELS DURING REMOVAL OF NEEDLE

[76] Inventor: Michael Porat, 52 Hamitnadev Street, Afoka, Tel Aviv 69690, Israel

[21] Appl. No.: 981,834

[22] PCT Filed: Jul. 26, 1996

[86] PCT No.: PCT/IL96/00067

§ 371 Date: Jan. 21, 1998

§ 102(e) Date: Jan. 21, 1998

[87] PCT Pub. No.: WO97/04821

PCT Pub. Date: Feb. 13, 1997

[30] Foreign Application Priority Data

Jul. 26, 1995 [IL] Israel .......................................... 114739

[51] Int. Cl.$^6$ .................................................. A61B 17/00
[52] U.S. Cl. ............................. 606/201; 602/58; 128/887
[58] Field of Search ..................................... 606/201, 202, 606/203, 204; 602/42, 45, 58, 52; 128/887, 888

[56] References Cited

U.S. PATENT DOCUMENTS 5,269,803 12/1993 Geary et al. ............................ 606/201
5,653,224 8/1997 Johnson ............................... 606/201 X Primary Examiner—Michael Buiz
Assistant Examiner—Vikki Trinh
Attorney, Agent, or Firm—Dennison, Meserole, Pollack & Scheiner

[57] ABSTRACT

A system and method for preventing the spurting of blood from a vein or artery, the system including an adhesive tape comprising an air permeable non-woven material, across the width of which an adhesive is applied in rows, and a hemostatic island absorbent dressing pad, which expands on contact with fluids, affixed to said non-woven material, and an armband associated with the adhesive tape, the armband including a flexible strap having a notched underside, a pressure box with a rigid extension on either side thereof attached to one end of the strap, the pressure box and extensions forming a T shape, a groove defined along the width of the strap where the strap is attached to one rigid extension, at one end of the T shape, to enable the strap to bend downwards at a 90° angle with respect to the rigid extension, and a ratchet device, through which the strap can be pulled in one direction, coupled to the other rigid extension, at another end of the T shape, such that applying the adhesive dressing over a hypodermic needle inserted into the vein or artery and pressing the pressure box on the armband over the island absorbent dressing pad enables removal of the needle and maintaining sufficient even pressure on the wound to prevent spurting of blood therefrom without cutting off circulation in the arm and without requiring the assistance of a nurse or attendant.

12 Claims, 3 Drawing Sheets

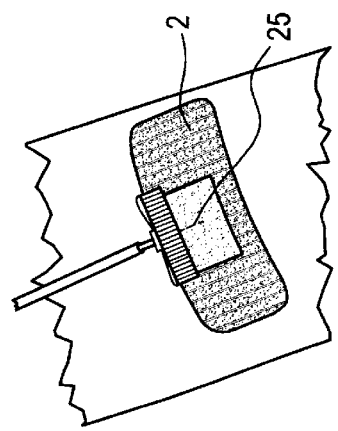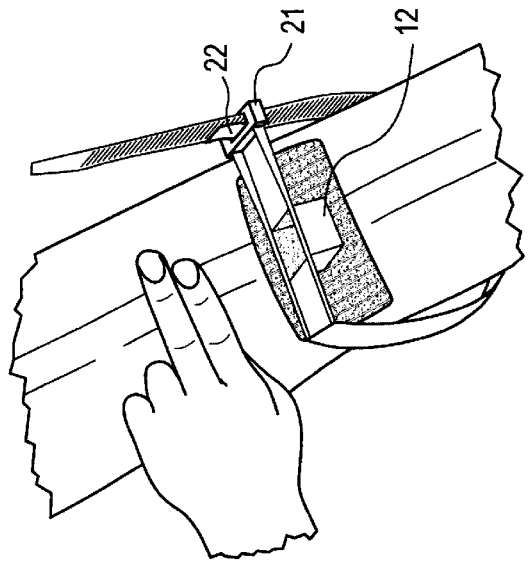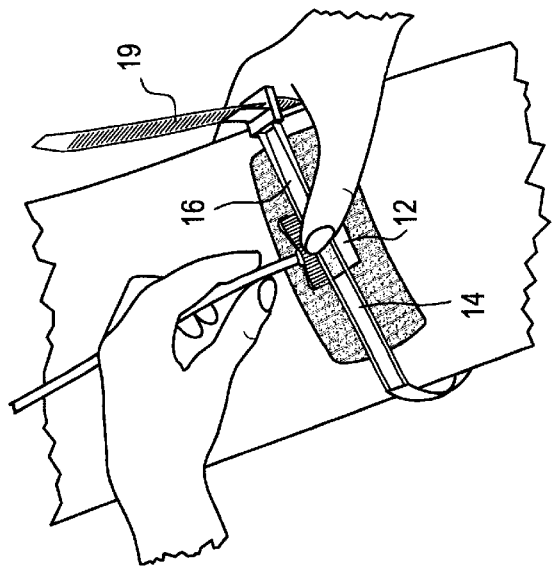

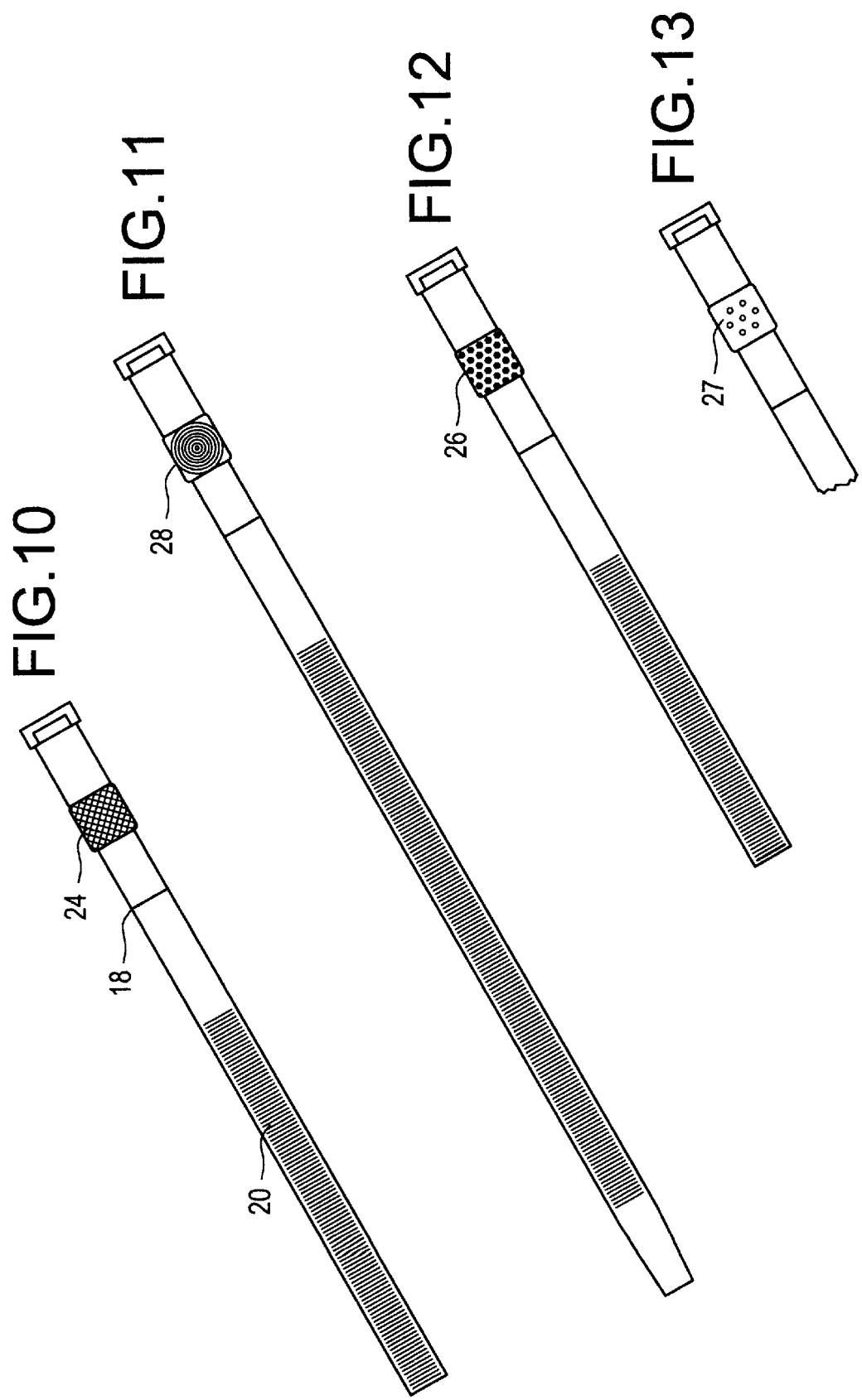

SYSTEM FOR PREVENTION OF BLOOD SPURTS FROM BLOOD VESSELS DURING REMOVAL OF NEEDLE

FIELD OF INVENTION

The present invention relates to a system for dressing the wound created during dialysis and preventing the spurting of blood from the blood vessel during and after removal of a hypodermic needle. The invention also relates to a novel strap means for applying pressure on a wound made by a hypodermic needle, particularly suitable for use in hemodialysis.

BACKGROUND

Hemodialysis, generally called simply dialysis, is a method for permanently maintaining patients whose kidneys have failed to function totally or almost totally because of disease or injury.

In healthy kidneys, blood flows through the kidney tubes where waste materials pass through the microscopically thin walls and are eliminated through the urine, while the cleansed and purified blood returns into circulation. Hemodialysis duplicates this process almost exactly. A dialysis machine is connected to an artery via an intake tube and the natural pumping action of the heart drives the blood into the machine, where it is passed through a semi-permeable membrane immersed in a specially prepared cleansing solution. The blood is then returned to the patient's body through another tube to a vein.

In most cases, where a person requires dialysis on a regular basis, a simple operation is performed, whereby a vein in the arm is connected to an artery. This creates a vein which is rich in arterial blood. The connecting tube is called a "shunt".

In order to perform the dialysis it is common to insert into the shunt, a hypodermic needle connected to a tube that leads to the dialysis machine. Between the metal part of the hypodermic needle and the tube is a plastic butterfly-wing shaped connection (hereinafter called "butterfly"). This enables easy insertion and removal of the needle.

The common practice is to insert the second needle for the return flow of the blood from the dialysis machine to the vein, close to the point of entry of the first needle (approximately 5 to 10 cm apart).

When the needle is removed from the shunt, blood spurts out due to the fact that the shunt is filled with arterial blood which is driven by pressure from the pumping action of the heart. To eliminate this spurting of blood, one has to exert pressure at the point of entry of the needle into the skin. This is done by pressing a sponge on the area. The sponge is usually a gauze ball or folded gauze pad and is held in place by pressing with a finger. The blood flow is stopped and the needle removed. The pressure is maintained on the skin, on the blood vessel and on the shunt below it until the shunt is closed by a blood clot and a clot forms on the skin—a process which can take from 5 to 30 minutes, depending on the individual patient. When the clots are formed, the sponge is removed and replaced with a clean dressing.

From the moment that the needle is removed until the end of the pressure process, the nurse/attendant must hold the sponge in place, and cannot release the pressure, thus taking valuable time which could be used to attend to another patient. The nurse/attendant is naturally impatient to complete the process, and may release the pressure on the sponge too early, to see if the blood has clotted. This results in uneven pressure being applied on the area which is unhealthy. When pressure is released before the proper time, blood clots are not properly formed and each further burst of blood enlarges the former clot. The shunt eventually becomes blocked by these excess clots and may have to be replaced.

There exist several methods for preventing blood spurting from the entry/exit point of the needle.

One such method involes applying a plastic (non-permeable) adhesive tape which contains in its center an expandable sponge pad to one side of the needle. The pad is positioned above the point of entry/exit of the needle and expands on contact with fluids. Pressure is exerted on the sponge pad under which lies the needle and the needle is removed by holding the butterfly on the needle. Continuous pressure is exerted on the sponge whilst the other half of the adhesive tape is adhered over the wound. Digital pressure continues until the shunt and the wound are dry. The pressure on the sponge is released and the patient is free to leave with the dressing adhered. Alternatively, when the nurse/attendant assumes that the hole in the shunt and the wound has healed, pressure is released. We are unaware of any system whereby the entire adhesive tape is adhered to the wound before the needle is removed. We have experimented and have found that in the presently used adhesive tapes the glue sticks to the needle and to the butterfly, which makes it difficult to remove the needle with ease, especially while a finger is exerting pressure on the center of the sponge (this is in fact an uneven pressure which may cause blood spurts).

Another method for preventing blood spurting is as follows:

A folded gauze sponge is placed above the needle. The needle is removed and instead of exerting digital pressure, one of the undermentioned methods is used:

a) An elastic bandage is rolled around the arm, creating pressure. This system is unsafe and is rarely used.

b) A mechanical clamp is applied on the gauze sponge. The clamp is similar to tongs whose curved arms are held together by a spring. These tongs replace the finger when the needle is removed and the nurse/attendant is free to attend to other patients. This is an expensive method—the life-span of the tongs is short because the spring does not last long. Risks of cross infection are prevalent because the tongs are re-usable.

c) A plastic arm strap is placed over the gauze sponge. The arm strap has a rough, notched surface along its underside with a ratchet device at one end, allowing the strap to be pulled through it in one direction. Attached to the ratchet device is a shoulder-shaped housing which fits over the sponge. The shoulders create pressure on the sponge and replace the previously used finger. The needle is removed by means of the butterfly and extra pressure is exerted by tightening the strap for a time period of between 5 to 30 minutes, depending on the patient. The strap is removed by means of a release clip on the ratchet.

There are several disadvantages in using this latter system.

First of all the arm strap acts like a belt, creating homogeneous pressure all around, on the sponge and around the entire arm. This may stop the free flow of venous blood, causing the arm to turn blue due to lack of sufficient blood supply. Secondly, the sponge and/or the shoulder shaped housing may slip from the exact spot where pressure is required. Moreover, in this method, when the sponge with the absorbed blood is removed, the entire dried clot attached to the sponge is pulled off, which may cause the wound to bleed again. Therefore, after the removal of the sponge, a new adhesive tape with a new sponge has to be placed on the wound.

The above described arm strap cannot be used with the adhesive tape having an expandable sponge as previously described, for the following reasons:

a) Because of its shape the strap does not exert pressure directly on the sponge beneath the adhesive tape.

b) The shoulder-shaped housing of the arm strap is shaped to fit over an ordinary gauze sponge and would slip on the smooth surface of the adhesive tape when the strap is tightened. It therefore does not facilitate steady pressure at the point of entry/exit of the needle.

c) The system whereby half the adhesive tape is adhered at first, and the second half only after removal of the needle, does not permit the use of the above arm strap together with known adhesive tapes.

d) The arm strap slips from the center of the pad whilst the needle is removed and insufficient pressure results in spurting of arterial blood.

SUMMARY OF THE INVENTION

It is an object of the present invention to provide a esystem for preventing spurting of blood from blood vessels during removal of a hypodermic needle.

Another object of the invention is to provide a specially designed adhesive tape for use in conjunction with a novel armband to prevent spurting of blood from blood vessels during removal of a hypodermic needle.

Yet another object of the invention is to provide a system and armband for use in dialysis which will free the nurse/attendant from maintaining pressure on the wound after removal of the hypodermic needle from the shunt.

Still another object of the invention is to provide a system for removal of the hypodermic needle from the shunt wherein an adhesive tape is applied prior to the removal of the needle and remains in position after the patient has completed the dialysis and is released.

A further object of the invention is to provide a system that eliminates blood clots in the shunt and prolongs its life-time compared with current systems.

There is thus provided in accordance with the present invention a system to prevent the spurting of blood from a vein or artery including an adhesive tape comprising an air permeable non-woven material, across the width of which an adhesive is applied in rows, and a hemostatic island absorbent dressing pad, which expands on contact with fluids, affixed to said non-woven material, and an armband associated with the adhesive tape, the armband including a flexible strap having a notched underside, a pressure box with a rigid extension on either side thereof attached to one end of the strap, the pressure box and extensions forming a T shape, a groove defined along the width of the strap where the strap is attached to one rigid extension, at one end of the T shape, to enable the strap to bend downwards at a 90° angle with respect to the rigid extension, and a ratchet device, through which the strap can be pulled in one direction, coupled to the other rigid extension, at another end of the T shape, such that applying the adhesive dressing over a hypodermic needle inserted into the vein or artery and pressing the pressure box on the armband over the island absorbent dressing pad enables removal of the needle and maintaining sufficient even pressure on the wound to prevent spurting of blood therefrom without cutting off circulation in the arm and without requiring the assistance of a nurse or attendant.

There is further provided in accordance with the invention a method for preventing the spurting of blood from a vein or artery during and after removal of a hypodermic needle therefrom, the method including the steps of centrally positioning over the point of penetration of the needle a hemostatic island absorbent dressing pad, which expands on contact with fluids, which is affixed to a hemostatic adhesive dressing made of an air permeable non-woven material across the width of which an adhesive is applied in rows, adhering the dressing around the point of penetration and the needle, releasably affixing an armband about the dressing and the vein or artery, by centrally positioning over the island absorbent pad over the point of needle penetration a flat-based pressure box with a rigid extension on either side thereof, the pressure box and extensions forming a T shape, one rigid extension being affixed to a flexible strap having a notched underside to form the armband, bending the strap downwards at a 90° angle with respect to the one rigid extension about a groove defined along the width of the strap where the strap is attached to the rigid extension, inserting and pulling the strap through a ratchet device coupled to the other rigid extension, at another end of the T shape, until the box exerts slight pressure on the pad of the dressing, preventing blood spurts, and removing the hypodermic needle while the armband maintains sufficient even pressure on the point of penetration to prevent spurting of blood therefrom without cutting off circulation in the arm.

DETAILED DESCRIPTION OF INVENTION

The system of this invention incorporates a special adhesive tape and armband. When used together, the hypodermic needle is removed without spurting of blood from the shunt. The nurse/attendant is not required to remain beside the patient to exert digital pressure on the sponge until the shunt and skin are closed and dry, and is free to attend to other patients.

Other important advantages in our system are as follows:

No blood clots are formed in the shunt and on the skin and blood bruising under the skin is prevented.

There are no blood spurts from under the sponge when it is removed.

The blood circulation continues through the arm while the armband is still pressed against the wound area, ensuring the free flow of enriched venous blood and preventing the arm from becoming blue.

BRIEF DESCRIPTION OF THE DRAWINGS

The invention will be better understood with reference to the drawings wherein:

FIG. 1 illustrates an adhesive dressing of the invention before coming in contact with fluid;

FIG. 2 illustrates the adhesive dressing of FIG. 1 after coming in contact with fluid;

FIG. 3 shows the adhesive dressing of the invention applied over an inserted hypodermic needle;

FIG. 8 shows an armband pressing on an adhesive dressing while a needle is being removed;

FIG. 9 illustrates an armband with pressure box pressing on the sponge of the adhesive dressing; and FIGS. 10 to 13 show arm bands with pressure boxes having different contact surfaces.

Referring to FIGS. 1 and 2, the new adhesive tape 1 of the invention shown from the inner side which has the adhesive, is made from non-woven material (a known material used in the production of adhesive tapes), which provides a fairly rough surface and permits free passage of air through the adhesive tape. The outer surface 2 of the non-woven material (see FIG. 3) is impregnated with a water resistant coating, whilst the inner surface 3 is impregnated with an adhesive coating. Preferably, the non-woven material will be elastic. A flat pad 4 of expanding absorbent material is placed on the center of the adhesive tape. The size of the pad should be from about 10 mm×10 mm to about 50 mm×50 mm, the preferred size being 20 mm×20 mm. A thin layer of perforated film 5 is coated onto the surface of the expanding pad 4 where it comes into contact with the skin. This allows penetration of blood, yet prevents formation of blood clots between the pad and the skin. An adhesive layer is applied in rows 6 across the width of the non-woven material. This row arrangement of adhesive assures a weaker adherence of the needle and butterfly to the non-woven material, yet does not significantly reduce the adherence of the tape to the skin. It is recommended that the adhesive be applied to 50% of the surface of the non-woven material in a staggered manner so that 50% of the material is covered by adhesive in the form of rows and the rest of the spaces in between are of the same size as the rows of adhesive but with no adhesive. The adhesive non-woven material surrounds the pad 4 on all four sides, creating an "island" dressing. The side 7 of the adhesive tape where the needle is removed should have a limited distance between the edge of the pad and the edge of the tape—i.e. the width of the adhesive on the side where the needle is removed should be not less than 4 mm and not more than 15 mm from the edge of the pad to the edge of the tape, and preferably should not exceed 10 mm from the edge of the pad to the edge of the tape.

Referring now to FIGS. 4 to 7, there is shown a flexible plastic armband 10. The armband 10 comprises a pressure box 12 having a base 13, the same size as the pad 4 (FIG. 1) or even slightly larger. The preferred size is 20 mm×20 mm, the same as the preferred size of the pad. On either side of the box 12 and integrally formed therewith are rigid flat extensions 14 and 16. These extensions 14 and 16 are provided with reinforcing ribs 15 and 17 along their entire length including under the pressure box 12 in order to assure their inflexibility. The extensions are approximately 2 cm to 3 cm long, enough to prevent them from bending.

Figure 4:
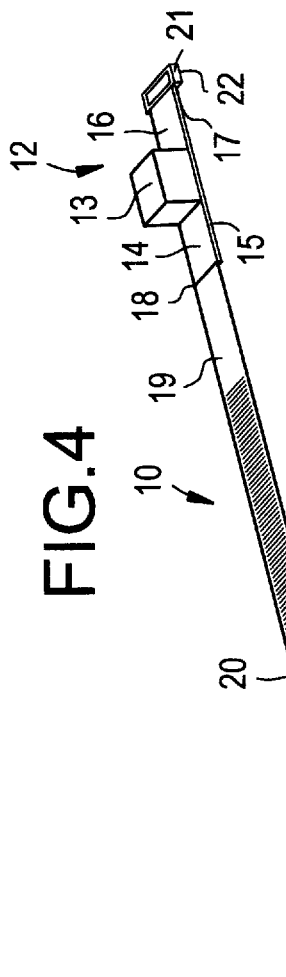
FIGS. 4 to 6 show respectively, perspective top, bottom and side views of an armband according to the invention.
Figure 5:
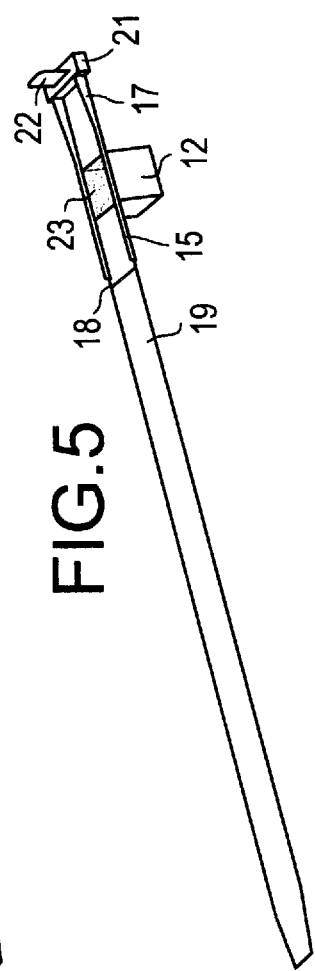
Figure 6:
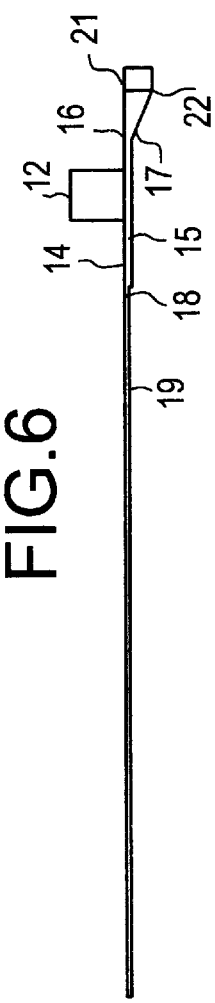
Figure 7:
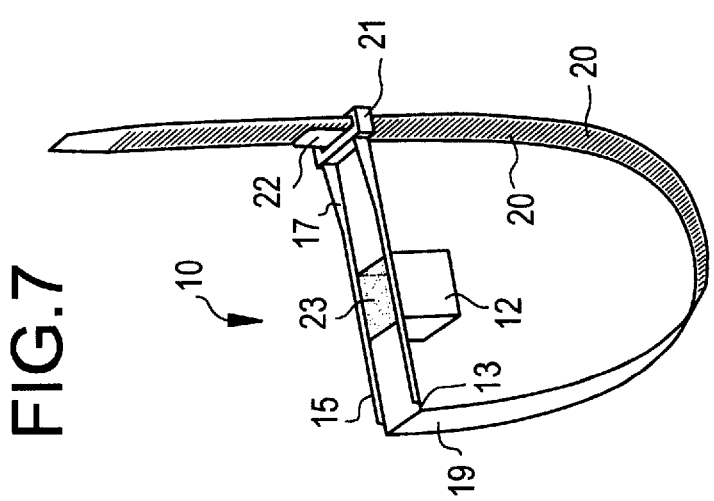
FIG. 7 illustrates the arm band as it is tied with the strap in the ratchet closure.

The pressure box 12 and the two ribbed extensions 14 and 16 thus form a rigid "T" shape. From one side of the extension 14 there extends integrally therewith a flexible strap 19. At the point where the extension 14 meets the strap 19 there is a groove 18 along the width of the strap 19 that allows the strap to bend downwards at a 90° angle (see FIG. 7). The underside of strap 19 has a notched surface 20. At the end of the other extension 16, there is a ratchet device 21 through which the strap 19 can be pulled in one direction. The ratchet 21 also includes a release clip 22 which, when pulled, releases the strap 19 from the ratchet 21.

The recommended height of the pressure box 12 is greater than 5 mm and preferably greater than 12 mm, with the length of the ribbed extensions being at least 25 mm on either side.

The use of the pressure box facilitates the exertion of pressure on the pad at its base, and the pressure is evenly distributed around the arm band which is wound around the arm of the patient. The areas of the skin under the two ribbed extensions are under no stress, allowing the free flow of venous blood, avoiding the phenomena of the arm becoming blue due to lack of enriched blood.

By means of the rigid T shape of the pressure box and extensions and the 90° angle of the strap on both sides of the T, equal stress is reached on both sides of the strap; on one side—the pressure box on the pad, and on the other side, the strap in contact with the skin. The stress of the strap around the arm is equal to the stress of the pressure box on the pad, but as the total surface area of the strap touching the arm exceeds the total surface area of the base of the box several times, the pressure reached is in direct proportion, e.g.—

$$P2 = \frac{W \times L \times P1}{C \times D}$$

where:

p1=pressure of the armband on skin under tension per mm$^2$

P2=pressure of the box on pad when armband is under tension per mm$^2$

S=stress

W=width of strap in mm

L=length in mm of strap in contact with the skin under tension

C=width of box in mm

D=length of box in mm

For example, if the strap is 15 mm wide, the length in contact with the skin under tension is 150 mm and pressure per sq. mm is 10 gr. (1 Kg. per sq. cm.) and the box is 20 mm wide and 20 mm long, then the pressure of the box (P2) per sq. mm is 56.25 gr. per mm$^2$:

$$P2 = 56.25 \text{ gr/mm}^2 = \frac{15 \times 150 \times 10}{20 \times 20}$$

In other words, if the pressure of the arm band on the skin is 1 Kg. per sqare centimeter, then the stress of the box on the pad is 22.5 Kg. and the pressure of the box on each square centimeter is 5.625 Kg.

Therefore, with steady light stress on the arm, we reach a multiplied higher pressure of the box on the flat pad under the adhesive tape.

The ideal situation of stronger pressure on the pad and lower pressure on the patient's arm is created.

The right T-shape of the pressure box and adjacent extensions enables easy removal of the needle, as will be described hereunder.

The recommended shape for the box is that it be hollow, tub shaped 23, for easier pressure on the center of the lower part of the box and economical material saving reasons.

To prevent slippage of the box on the surface of the adhesive tape, it is recommended that the base 13 of the box not be smooth, but rather have a rough surface 24 (see FIG. 10), which will stick to the tape. The surface can be roughened like sandpaper 26 (FIG. 12), or by means of small spikes 27 (FIG. 13) or round grooves 28 (FIG. 11) of sharp plastic. It is also recommended to coat the surface of the base with a light adhesive which will adhere to the tape and prevent slippage.

Method of Use:

When the dialysis session is completed, the nurse/attendant removes all the tapes from the butterfly and the needle and places the adhesive tape with the expandable pad over the needle 25, ensuring that the center of the pad is placed at the point of needle penetration (FIG. 3). The armband 10 is folded at the groove 18 at 90° and placed around the patient's arm, with the base of the pressure box over the center of the pad in the center of the island dressing 4. The means to prevent slippage from the adhesive tape will keep the box on the flat pad. The strap 19 is passed through the clip 21 and pulled carefully so that the box exerts slight pressure on the pad (replacing the conventional finger pressure), thus preventing blood spurts. The nurse/attendant exerts digital pressure on the center of the box, and with the free hand, firmly extracts the needle by means of the tube (FIG. 8).

Although the butterfly may adhere to the tape, trials conducted show that the needle can be easily removed, even when it appears to be held by the tape.

After the removal of the needle, the nurse/attendant pulls and fixes the strap 19 gently to ensure permanent pressure. The attendant should check the patient's pulse, and if necessary, gently release the pressure by a small tug on the strap release clip 22 (FIG. 9).

Immediately after the final fixing of the arm band, the patient is free to vacate the dialysis chair for another patient without fear of pressure release or slippage and no blood will leak from the shunt.

The armband is left in place for as long as it takes for the particular patient to stop bleeding, allowing an additional two minutes as a safety precaution. After the removal of the strap, the adhesive island dressing remains as a protection on the wound where the needle was removed. It will remain in place, preventing the spurting of capillary blood due to its high absorbency, expanding and non-adherent feature. It can be removed at least one hour after removal of needle.

The combination of steady pressure from the centered pressure box with rigid extensions and the immobility of the expanding non-adherent island pad on the adhesive dressing until the first original clots in the shunt and skin are completely dry, reduces blood clots which could block the shunt.

It will be appreciated by those skilled in the art that the invention is not limited to what has been shown and described hereinabove by way of example. Rather, the scope of the invention is defined solely by the claims which follow.

I claim:

1. A system to prevent the spurting of blood from a vein or artery comprising:
    a) an adhesive tape comprising an air permeable non-woven material, across the width of which an adhesive is applied in rows, and a hemostatic island absorbent dressing pad, which expands on contact with fluids, affixed to said non-woven material; and
    b) an armband associated with said adhesive tape, said armband comprising:
        1) a flexible strap having a notched underside;
        2) a pressure box with a rigid extension on either side thereof attached to one end of said strap, said pressure box and said extensions forming a T shape;
        3) a groove defined along a width of the strap where the strap is attached to one rigid extension, at one end of the T shape, to enable the strap to bend downwards at a 90° angle with respect to the rigid extension; and
        4) a ratchet device, through which the strap can be pulled in one direction, coupled to the other extension, at another end of the T shape;
    such that applying the adhesive dressing over a hypodermic needle inserted into the vein or artery and pressing the pressure box on the armband over the island absorbent dressing pad enables removal of the needle and maintaining sufficient even pressure on the wound to prevent spurting of blood therefrom without cutting off circulation in the arm and without requiring the assistance of a nurse or attendant.

2. The system as in claim 1, wherein each said rigid extension comprises reinforcing ribs to ensure its rigidity.

3. The system as in claim 1, wherein the pressure box on the armband includes a flat base having means to prevent slippage of said base from the adhesive tape.

4. The system as in claim 1, wherein the ratchet device includes a release clip.

5. The system as in claim 1, wherein the absorbent dressing pad is non-adherent to blood clots or wounds.

6. An armband suitable for preventing the spurting of blood from a vein or artery comprising:
    a) a flexible strap having a notched underside;
    b) a pressure box with a rigid extension on either side thereof attached to one end of said strap, said pressure box and extensions forming a T shape;
    c) a groove defined along the width of the strap where the strap is attached to one rigid extension, at one end of the T shape, to enable the strap to bend downwards at a 90° angle with respect to the rigid extension; and
    d) a ratchet device, through which the strap can be pulled in one direction, coupled to the other rigid extension, at another end of the T shape.

7. The armband as in claim 5, wherein each said rigid extension comprises reinforcing ribs to ensure its rigidity.

8. The armband as in claim 5, wherein the pressure box on the armband includes a flat base having means to prevent slippage of said base from the adhesive tape.

9. The armband of claim 8, wherein said means to prevent slippage is selected from a rough surface, small spikes, grooves and an adhesive coating.

10. The armband of claim 5, wherein the ratchet device includes a release clip.

11. A method for preventing the spurting of blood from a vein or artery during and after removal of a hypodermic needle therefrom, the method comprising steps of:
    a) centrally positioning over a point of penetration of the needle a hemostatic island absorbent dressing pad, which expands on contact with fluids, which is affixed to a hemostatic adhesive dressing made of an air permeable non-woven material across a width of which an adhesive is applied in rows;
    b) adhering said dressing around the point of penetration and the needle;
    c) releasably affixing an armband about said dressing and the vein or artery, by centrally positioning over said island absorbent pad over the point of needle penetration a flat-based pressure box with a rigid extension on either side thereof, said pressure box and extensions forming a T shape, one rigid extension being affixed to a flexible strap having a notched underside to form said armband;
    d) bending said strap downwards at a 90° angle with respect to said one rigid extension about a groove defined along the width of the strap where the strap is attached to said rigid extension;
    e) inserting and pulling said strap through a ratchet device coupled to the other rigid extension, at another end of the T shape, until the box exerts slight pressure on the pad of the dressing, preventing blood spurts; and
    f) removing the hypodermic needle while said armband maintains sufficient even pressure on the point of penetration to prevent spurting of blood therefrom without cutting off circulation in the arm.

12. The method of claim 11, further comprising the step of providing means to prevent slippage of said pressure box from said island absorbent pad before said step of releasably affixing.

* * * * *